United States Patent [19]

Sprecker et al.

[11] 4,162,256

[45] Jul. 24, 1979

[54] PROCESS FOR THE PRODUCTION OF COMPOUNDS USEFUL IN PERFUMERY

[75] Inventors: Mark A. Sprecker, Sea Bright; Ernst T. Theimer, Rumson, both of N.J.

[73] Assignee: International Flavors & Fragrances Inc., New York, N.Y.

[21] Appl. No.: 897,903

[22] Filed: Apr. 19, 1978

[51] Int. Cl.$^2$ .................... C07D 311/04; C07C 49/76
[52] U.S. Cl. ................................. 260/345.2; 260/592; 252/522
[58] Field of Search ..................................... 260/345.2

[56] References Cited

U.S. PATENT DOCUMENTS

| | | | |
|---|---|---|---|
| 3,360,530 | 12/1967 | Heeringa et al. | 260/345.2 |
| 3,532,719 | 10/1970 | Theimer | 260/345.2 |
| 3,910,964 | 10/1975 | Sanders et al. | 260/345.2 |
| 4,066,648 | 1/1978 | Oka et al. | 260/345.2 |

Primary Examiner—Nicky Chan
Attorney, Agent, or Firm—Arthur L. Liberman; Franklin D. Wolffe

[57] ABSTRACT

Process for producing compounds useful in perfumery including isochromans and acylated indane hydrocarbons with an alkylene oxide or with a lower acyl halide in the presence of a hydrocarbon or hydrocarbon mixture containing $C_5$ to $C_{10}$ alkanes at a temperature of from $-20°$ C. up to $-5°$ C. In the case of forming isochromans, the resulting alcohol is reacted, in situ, with a lower alkanol and a formaldehyde precursor at temperatures of from $20°$ C. up to $80°$ C.

7 Claims, 2 Drawing Figures

GLC PROFILE

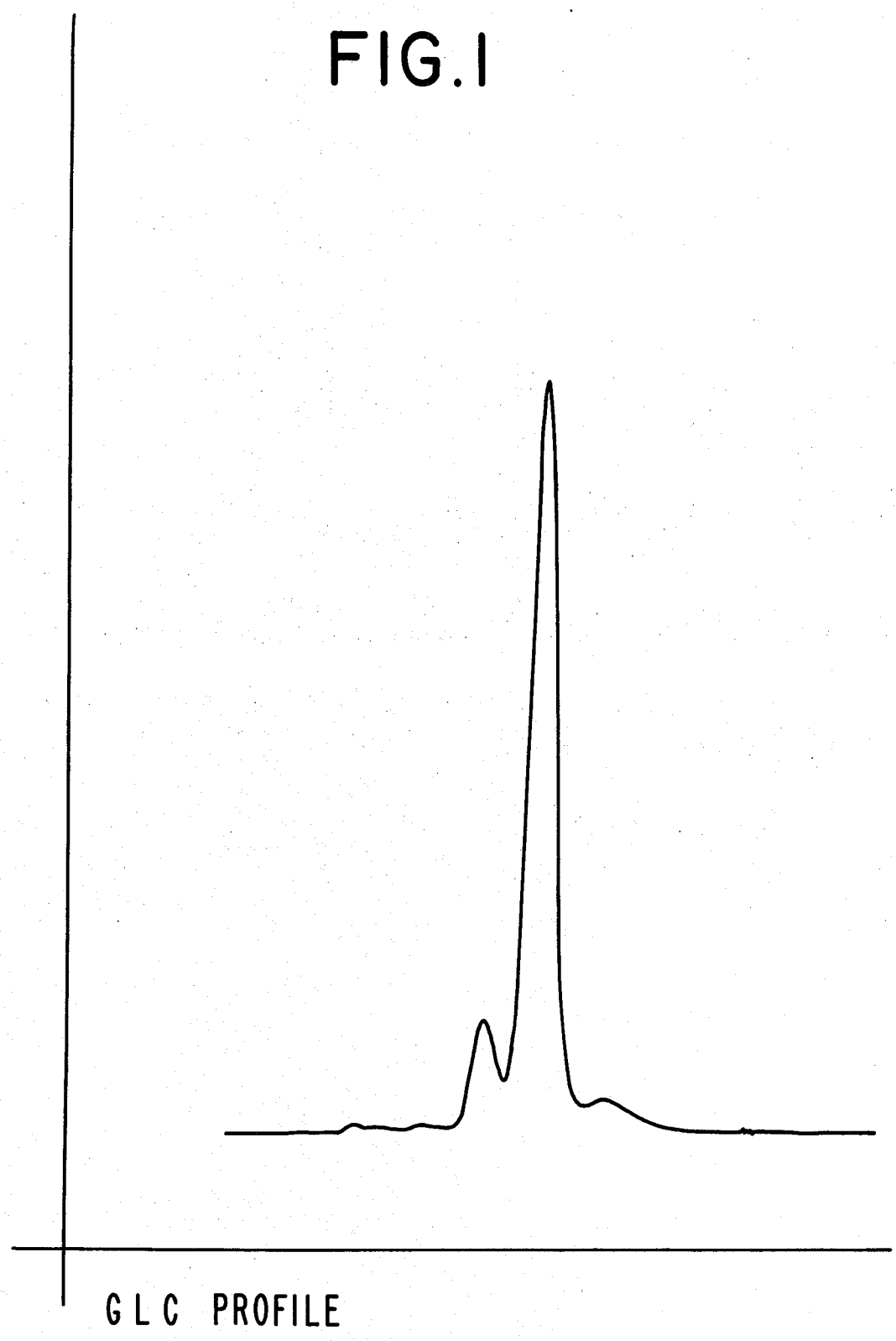

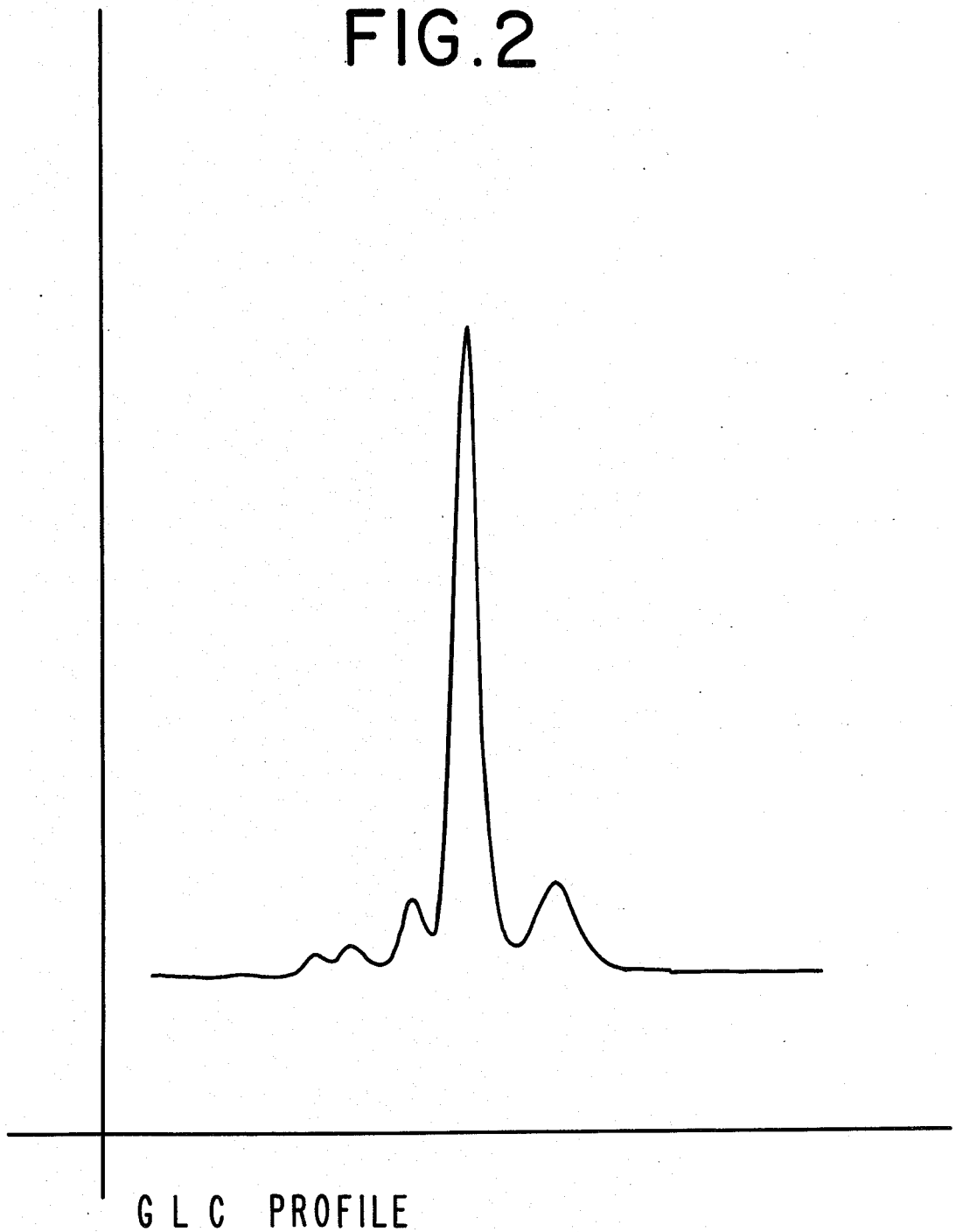

PROCESS FOR THE PRODUCTION OF COMPOUNDS USEFUL IN PERFUMERY

BACKGROUND OF THE INVENTION

The production of isochromans has been shown in the art and certain novel isochromans have recently been disclosed with an outstanding musk fragrance. Such isochromans especially adapted for perfumery by virtue of their fragrance properties have been disclosed in Heeringa & Beets U.S. Pat. No. 3,360,530, issued on Dec. 26, 1967.

A number of routes are available for the production of isochromans, such as those set forth in U.S. Pat. No. 3,360,530 and one of the most straightforward of these routes is treatment of a Friedel-Crafts reactant with an alkylene oxide under Friedel-Crafts conditions to form an aryl alkanol. The aryl alkanol is then isolated and thereafter reacted with formaldehyde to cyclialkylate the alcohol. The efficiency of this multi-stage process leaves much to be desired because of a number of discreet processing steps and extended working times which also results in considerable yield impairment.

U.S. Pat. No. 3,532,719 sets forth a process for producing such isochromans which solved a number of the problems of the processes set forth in U.S. Pat. No. 3,360,530. U.S. Pat. No. 3,532,719 provided a more simplified and more economical process for producing isochromans which comprises reacting a Friedel-Crafts reactant with an alkylene oxide in the presence of aluminum chloride in a chlorinated hydrocarbon solvent to form, in situ, an aryl alkanol-aluminum chloride complex; partially deactivating the aluminum chloride after formation of the aryl alkanol complex; and cyclialkylating the contained aryl alkanol with formaldehyde or a formaldehyde equivalent in the presence of the partially deactivated aluminum chloride to form, upon quenching, the isochroman. The disadvantage of such procedures for the preparation of isochromans is the use of halogenated hydrocarbon solvents, many of which are expensive and have been reported to be health hazards. The use of halogenated benzene derivatives require very low temperatures −40° C. to −30° C. in order to obtain the best yields. The maintenance of such low temperatures for an extremely exothermic reaction requires the installation of expensive processing equipment and extended reaction times, which can impair yields.

Steyn and Holzapfel, *Tetrahedron*, 23 4449 (1967), reports the reaction of a halo aryl alkanol with chloromethyl methyl ether and zinc chloride to give an isochroman according to the following reaction:

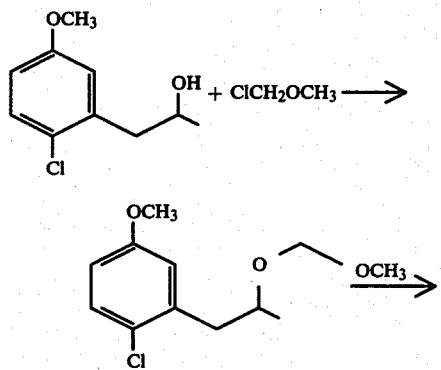

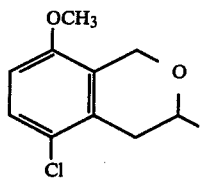

Meyer and Turner, *Tetrahedron*, 27 2609 (1971), reports the reaction of a methoxy aryl alkanol with sodium hydride and chloromethyl methyl ether to give a methoxy aryl alkanol methyl ether. Subsequent treatment of the methoxy aryl alkanol methyl ether with toluenesulfonic acid is indicated to yield isochromans according to the following reaction:

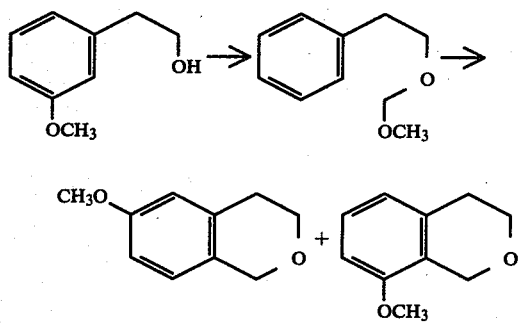

The disadvantages of such processes include the utilization of chloromethyl methyl ether which has been reported to be a health hazard. Also, several distinct processing steps are needed to form the isochroman ring, compared to the simplicity of a single processing step in the instant invention.

In order to overcome the problems of the prior art U.S. Pat. No. 3,910,964 issued on Oct. 7, 1975 and U.S. Pat. No. 3,978,090 issued on Aug. 31, 1976 covered a process for producing isochromans having the structure:

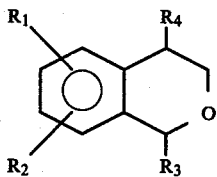

wherein $R_1$ and $R_2$ are each (i) separately selected from the group consisting of hydrogen, lower alkoxy, lower alkyl, and, (ii) taken together, selected from the group consisting of benzo, cyclopentano, cyclohexano, naphtho, monoalkyl cyclopentano, polyalkyl cyclopentano, monoalkyl cyclohexano and polyalkyl cyclohexano, and $R_3$ and $R_4$ are the same or different and are selected from the group consisting of hydrogen and lower alkyl comprising the steps of intimately admixing:

(A) An alkanol having the structure:

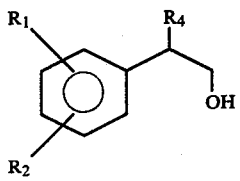

(B) An acetal having the structure:

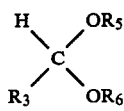

(wherein $R_5$ and $R_6$ are alkyl;

(C) A protonic acid selected from the group consisting of p-toluene sulfonic acid and phosphoric acid; and (D) An azeotroping agent selected from the group consisting of n-hexane, cyclohexane, methyl cyclohexane, benzene and toluene; and simultaneously (i) heating the resulting mixture of a period of time whereby a substantial amount of the isochroman having the above structure is formed while (ii) azeotropically removing water of reaction with the azeotroping agent.

However, the processes of U.S. Pat. Nos. 3,910,964 and 3,978,090 require isolation of the aryl alkanol resulting from the Friedel-Crafts reaction, and subsequent conversion, in a separate step, to the cyclialkylated isochroman. These two step processes require significantly more processing time and processing equipment compared to the efficient one step method of the instant invention.

Prior to the instant invention, synthetic musks such as 5-acetyl-1,1,2,3,3,6-hexamethylindane having the structure:

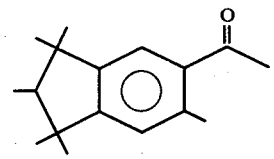

and 6-acetyl-1,1,3,4,4,6-hexamethyltetrahydronaphthalene were produced using several complicated and low-yield processes. Arctander, "Perfume and Flavor Chemicals (aroma chemicals)" published by the author in 1969, volume I, Monographs numbers 40 and 41 discloses such acylated indane musks.

The use of six, seven or eight carbon saturated hydrocarbons as solvents in order to aid Friedel-Crafts catalysis is disclosed at column 3, lines 5–10 of the U.S. Pat. No. 3,439,056 but the nature of the reaction (conversion of a first type of acylcyclic compound to a second type of acylcyclic compound using a specific catalyst) is different in kind from the reaction of the instant invention.

THE INVENTION

The present invention provides a simplified, economical process for producing synthetic musks such as isochromans and acylated indanes and acylated tetrahydronaphthalenes using an economical process involving the use of one reactor and one physical step. More specifically, the present invention provides a process for preparing isochromans having the structure:

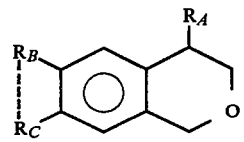

wherein $R_B$ and $R_C$, taken together, form a substituted or unsubstituted cycloalkano ring and $R_A$ is hydrogen or methyl, for example the isochroman "Galaxolide ®" (a trademark registered in the U.S. Patent Office owned by International Flavors & Fragrances Inc.) having the structure:

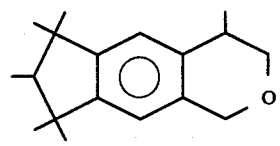

and "Musk 89" having the structure:

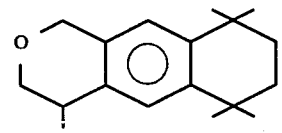

comprising the step of intimately admixing an indane derivative such as a pentamethylidane having the structure:

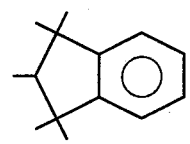

or a hexahydrotetramethylnaphthalene having the structure:

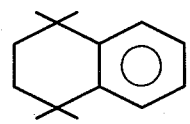

with aluminum chloride and an alkylene oxide such as propylene oxide in the presence of an alkane or alkane mixture comprising $C_5C_{10}$ hydrocarbons such as isooctane (2,2,4 trimethyl pentane), n-hexane or n-octane. This part of the reaction occurs at temperatures from $-20°$ C. up to $-5°$ C. with the alkane: pentamethyl indane weight ratio being from 1:10 up to 10:1 with a weight ratio of 0.2:1 up to 0.3:1 being preferred. A mole ratio of aluminum chloride: alkylene oxide (e.g. propylene oxide) may vary from 1:2 up to about 2:1 with a mole ratio of 1:1 up to 1.02:1 being preferred. The mole ratio of pentamethyl indane:alkylene oxide may vary from 1:1 up to 10:1 with a mole ratio of 2:1 being preferred. In the second part of the reaction, in the same reactor, a lower alkanol (e.g. isobutanol, ethanol or isopropanol) is added to the reaction mass in order to deactivate the aluminum chloride, preferably at temperatures below 0° C., followed by the addition of a formaldehyde precursor such as paraformaldehyde, di-isopropylformal or di-methoxy methane. The temperature at this point of the process of our invention may vary from 20° C. up to about 80° C. with a temperature of 40° C. being preferred. Such a temperature gives rise to a convenient rate of reaction yet still permits a high yield of isochroman to be formed. The mole ratio of lower alkanol such as isopropanol to aluminum chloride is preferably 1:1. The mole ratio of formaldehyde precursor: propylene oxide is preferably 1:1.

Although 1,1,3,3-pentamethylindane and 1,1,4,4 tetramethyltetrahydronaphthalene are the primary precursors, these compounds, for example, the pentamethyl indane, may be admixed with other compounds resulting from the reaction of, for example, alpha methyl styrene and t-amyl alcohol or t-amylene such as those having the structures:

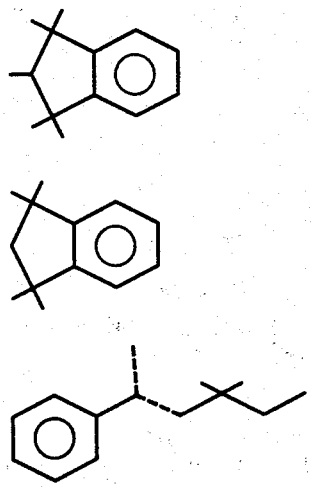

wherein one of the dashed lines is a carbon carbon single bond and the other of the dashed lines is a carbon carbon double bond.

In forming the isochromans, for example, 'Galoxolide,' the mechanism of the reaction is as follows:

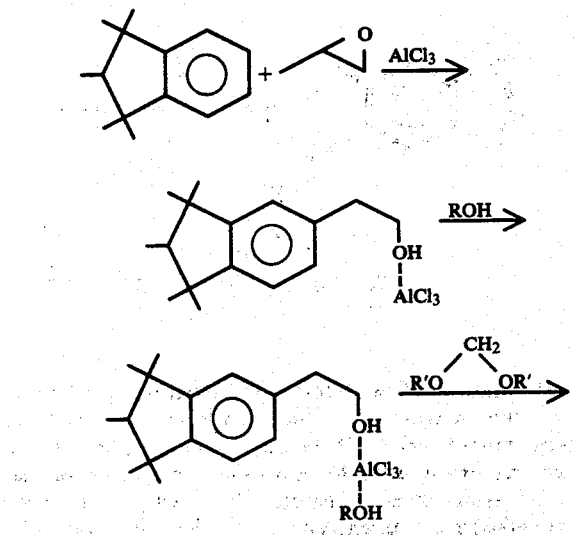

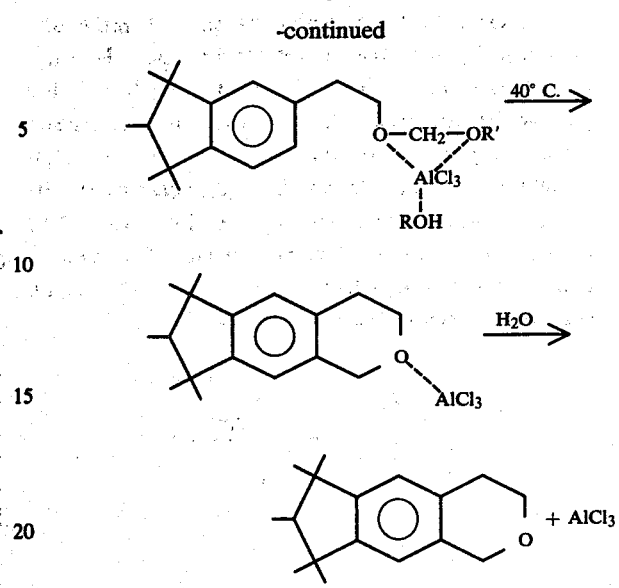

wherein R and R' are the same or different lower alkyl such as methyl, ethyl, i-propyl or i-butyl. After the reaction to form the isochroman, the reaction mass is quenched by pouring into water, discarding the aqueous phase (containing AlCl₃) and neutralized with aqueous base such as dilute sodium hydroxide or potassium hydroxide solution. The washed mixture is then treated by conventional techniques such as distillation, extraction, preparative chromotography and the like to obtain a highly purified isochroman. Fraction distillation is a preferred method of purifying the isochroman.

The Galaxolide ® produced according to our invention is from an organoleptic standpoint, a product superior to that produced according to the methods of the prior art in that it contains a major odoriferous isomer which causes the resulting product to be at least 20% stronger than any prior art Galaxolide ® products. This can be determined from a comparison of the major peak of the GLC profiles in FIGS. 1 and 2. The major peak comprises the major odoriferous component in each case.

In forming other synthetic musks, in place of the alkylene oxide which would be reacted with, for example, 1,1,2,3,3-pentamethylidane or with the 1,1,4,4-tetramethyltetrahydronaphthalene, an acyl halide such as acetyl chloride may be reacted with the pentamethylindane or hexahydronaphthalene derivative in order to form compounds having the structures:

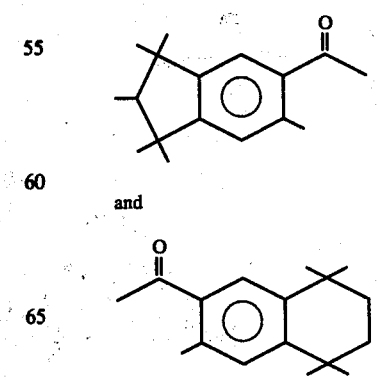

In carrying out the acylation reaction, the mole ratio of indane hydrocarbon or tetrahydronaphthalene hydrocarbon to acyl halide is from 1:1 up to 10:1 with a ratio of 2:1 preferred. The mole ratio of hydrocarbon solvent, e.g. n-hexane, n-octane or isooctane (2,2,4-trimethyl pentane), to tetrahydronaphthalene hydrocarbon or indane hydrocarbon may be from 1:10 to 10:1 with a ratio of 2:10 to 3:10 being preferred. The reaction temperature may vary from −20° C. up to −5° C. The reaction in generic terms is as follows:

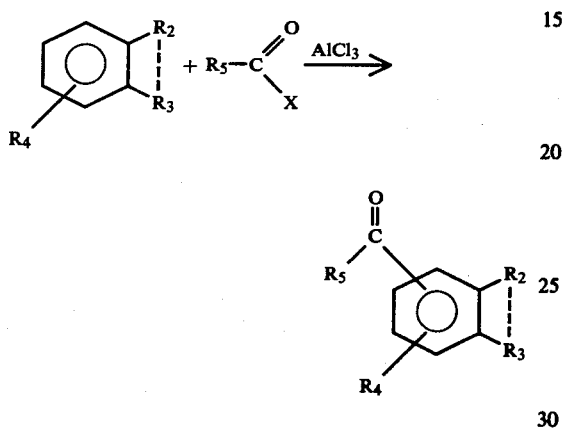

wherein $R_4$ is ethyl or methyl, and $R_2$ and $R_3$ complete a polyalkylated cyclohexano or cyclopentano moiety whereby a polyalkylated indane group is present or whereby a polyalkylated tetrahydronaphthalene group is present; and $R_5$ is methyl, ethyl or isopropyl. Examples of reactions within the scope of this invention are as follows:

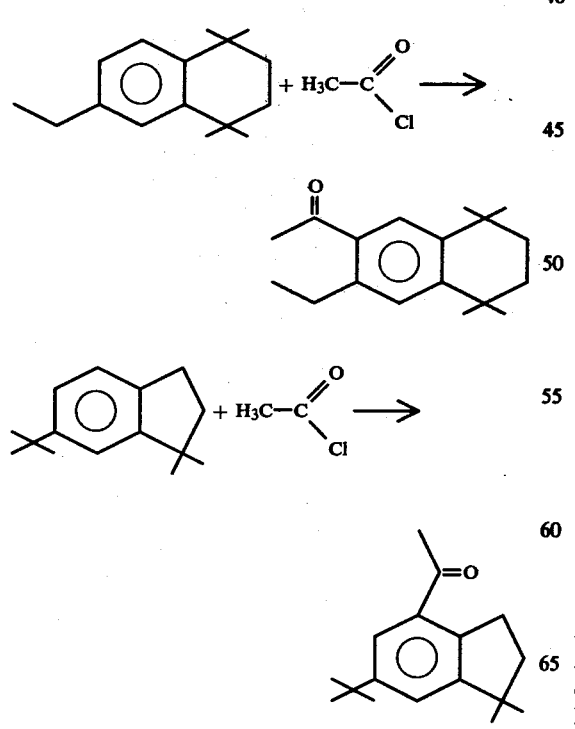

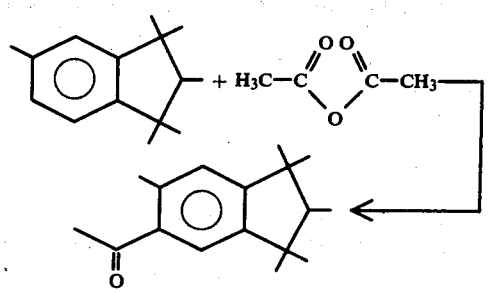

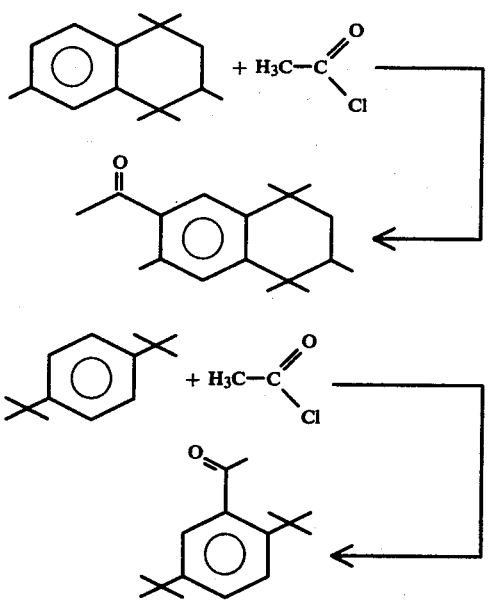

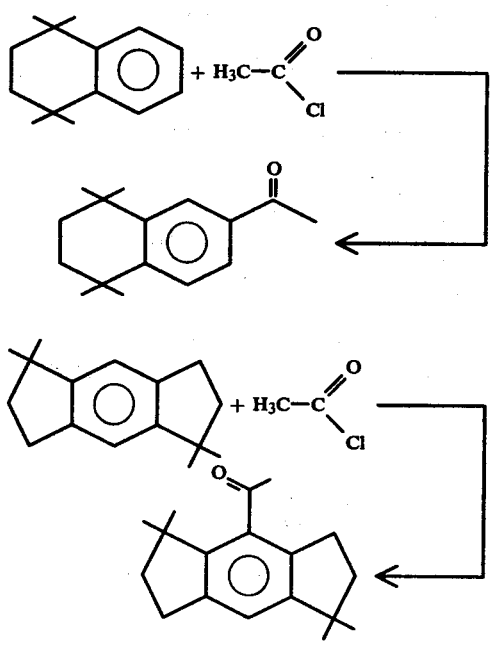

It is the use of the aliphatic saturated hydrocarbon in conjunction with the Friedel-Crafts reactant and the aluminum chloride which causes the reaction mass to decrease in viscosity, thereby improving dispersion and heat transfer. Improved yields of desired product in the foregoing reaction sequences are achieved by minimizing the undesirable side reactions and shortening overall reaction times.

The following Examples are given to illustrate embodiments of the invention as it is presently preferred to practice. It will be understood that these Examples are illustrative and the invention is not to be considered as restricted thereto except as indicated in the appended claims.

EXAMPLE I 4,5,5,6,7,7-Hexamethyl-1H-Indano[2,3-C]Pyran (Galaxolide)

Reaction:

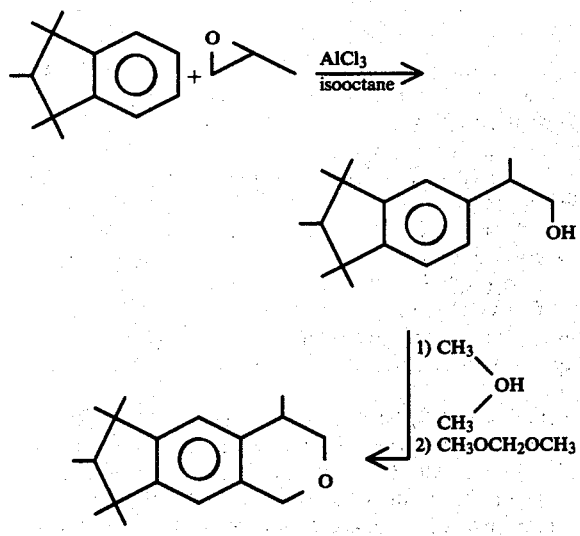

A solution of 388 grams of 1,1,2,3,3-pentamethylindane and 152 grams of propylene oxide is added over a 2½ hour period to a stirred slurry of 720 grams of 1,1,2,3,3-pentamethylindane, 360 grams of aluminum chloride, and 242 grams of isooctane at $-10°$ C. to $-5°$ C. At the end of this period, 194 grams of isopropyl alcohol is added to the reaction mixture over a ten minute period while retaining a temperature between $-5°$ C. and $0°$ C. External cooling is removed, and 251 grams of dimethoxymethane is added to the reaction mass. The reaction mass is then heated up to $50°$ C. and maintained at that temperature for a period of 2 hours. The reaction mass is then poured onto 4 liters of crushed ice with 2 liters of water and stirred for a period of 15 minutes. The reaction mass is then washed with a 2 liter volume of water followed by a 1 liter portion of dilute sodium hydroxide (5%). The reaction mass is then distilled after adding thereto 30 grams primol® yielding 239 grams of recovered isooctane (vapor temp. $32°$ C.–$45°$ C. at 35 mm vacuum); 875 grams of recovered 1,1,2,3,3-pentamethylindane (vapor temp. $70°$ C. to $110°$ C. at vacuum of 3 mm); and 304 grams of the product, 'Galoxolide' (vapor temp. $127°$ C. to $136°$ C., at vacuum of 2 mm).

The yield of product based on propylene oxide is 44%. The yield based on consumed 1,1,2,3,3-pentamethylindane is 95%.

EXAMPLE II 1,1,2,3,3-Pentamethyl-5-(β-Hydroxyisopropyl)Indane

Reaction:

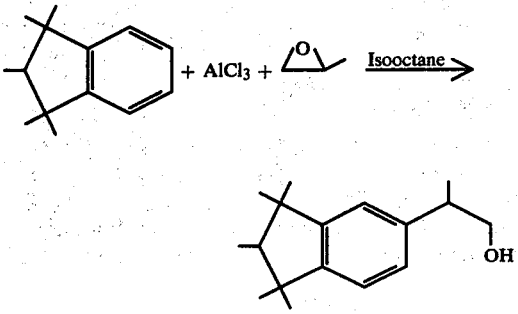

A solution of 431 grams of 1,1,2,3,3-pentamethylindane and 152 grams of propylene oxide are added over a 2½ hour period to a stirred slurry of 800 grams of 1,1,2,3,3-pentamethylindane, 246 grams of isooctane, and 360 grams of aluminum chloride at $-10°$ C. At the end of the addition, the reaction is poured into ice water. The organic layer is washed with water, then washed with dilute base.

Distillation through a 2 inch column affords 924 grams of 1,1,2,3,3-pentamethylindane and 271 grams of 1,1,2,3,3-pentamethyl-5-β-hydroxyisopropylindane (b.p. $165°$ at 2 mm).

The yield of product is 100% based on consumed pentamethylindane and 42% based on propylene oxide.

EXAMPLE III 4,5,5,6,7,7-Hexamethyl-1H-Indano[2,3-C]Pyran-'Galaoxide'

Reaction:

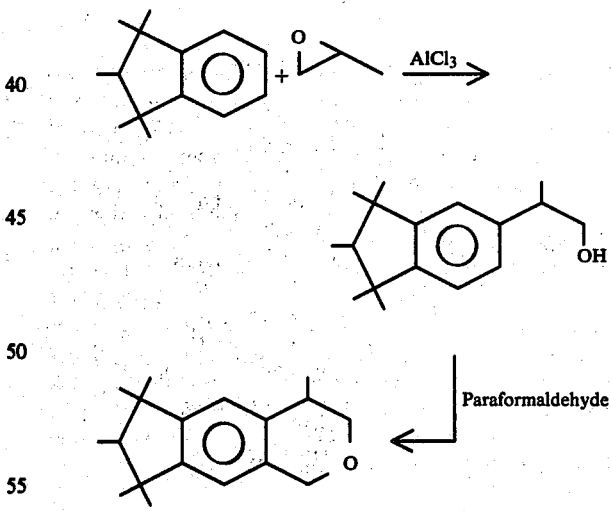

A solution of 300 grams of 1,1,2,3,3-pentamethylindane and 152 grams of propylene oxide is added over a 2½ hour period to a stirred slurry of 700 grams of isooctane, 489 grams of 1,1,2,3,3-pentamethylindane, and 360 grams of aluminum chloride at $-5°$ C. During the addition, the reaction mass becomes thick and 300 grams of toluene are added after the first hour. At the end of the addition, 162 grams of isopropanol are added to the reaction mass at $0°$ C. External cooling is removed, and 90 grams of paraformaldehyde are added to the reaction mass. The reaction mass is then heated to reflux ($80°$ C.)

and maintained at that temperature for a period of 2 hours.

The reaction mass is then poured onto 6 liters of ice water and stirred for 15 minutes. The organic layer is then washed with 2 liters of water followed by 1 liter of dilute sodium hydroxide solution.

The organic solution is distilled to afford recovered isooctane and toluene; 412 grams of recovered 1,1,2,3,3-pentamethylindane and 190 grams of product (27% yield based on propylene oxide. In addition, 143 grams of higher boiling and non-distillable material is recovered.

EXAMPLE IV 4,5,5,6,7,7-Hexamethyl-1H-Indano[2,3-C]Pyran-'Galaxolide'

Reaction:

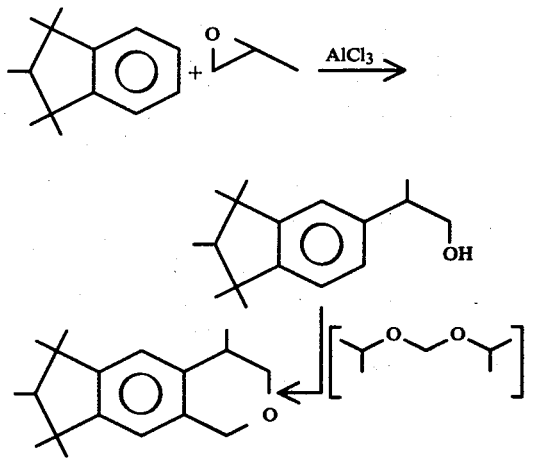

A solution of 431 grams of 1,1,2,3,3-pentamethylindane and 152 grams of propylene oxide are added over a 2½ hour period to a stirred slurry of 246 grams of isooctane, 800 grams of 1,1,2,3,3-pentamethylindane, and 360 grams of AlCl₃ at −10° C. At the end of the addition period, 162 grams of isopropanol are added to the reaction mass at −5° C. to −9° C. External cooling is removed and 205 grams of diisopropylformal are added. The reaction mass is heated to 40° and stirred for 2 hours. At the end of this time, the reaction mass is poured into ice water. The organic layer is washed and neutralized with dilute caustic soda. Distillation affords 1013 grams of recovered 1,1,2,3,3-pentamethylindane and 301 grams of product (43% yield based on propylene oxide; 98% yield based on consumed 1,1,2,3,3-pentamethylindane.

EXAMPLE V 3,4,6,7,8,9-Hexahydro-4,6,6,9,9-pentamethyl-1H-Naphthalene[2,3-C]Pyran-'Musk 89'

Reaction:

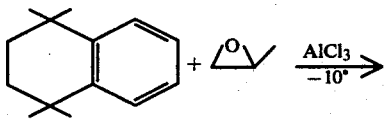

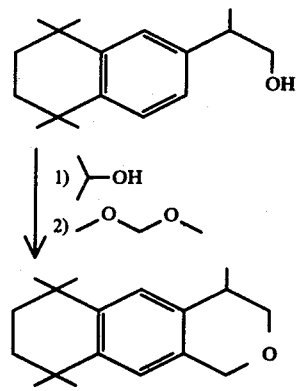

A solution of 388 grams of 1,1,4,4-tetrahydro-1,1,4,4-tetramethylnaphthalene and 152 grams of propylene oxide is added over a 2½ hour period to a stirred slurry of 360 grams of aluminum chloride, 720 grams of 1,1,4,4-tetrahydro-1,1,4,4-tetramethylnaphthalene, and 399 grams of isooctane at 70° C. At the end of this period, 162 grams of isopropanol are added at −10° C. External cooling is removed and 206 grams of dimethoxymethane is added. The reaction mass is heated to 40° C. for 2 hours. At the end of this time, the reaction mass is poured into ice water with stirring. The organic layer is washed with water and then washed with dilute base.

Distillation of the organic solution affords recovered solvent, 1029 grams of recovered 1,1,4,4-tetrahydro-1,1,4,4-tetramethylnaphthalene (b.p. 122°–134°, vac. 3 mm) and 226 grams of product (b.p. 140°–175°, 1.5 mm).

The yield of product, 'Musk 89', is 33 ½% based on propylene oxide and 91% based on consumed 1,1,4,4-tetrahydro-1,1,4,4-tetramethylnaphthalene.

EXAMPLE VI

4-Acetyl-6-t-Butyl-1,1-Dimethylindane

Reaction:

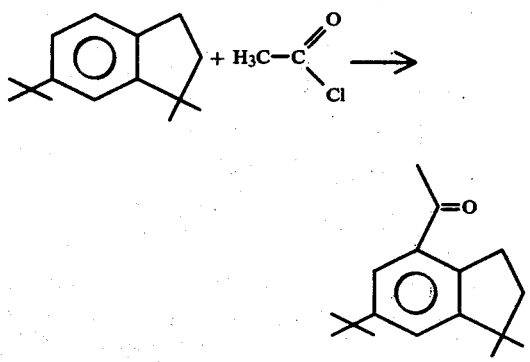

A solution of 1,1-dimethyl-6-t-butylindane (600 grams) and acetyl chloride (314 grams) is added over a 4 hour period at −10° C. to a slurry of aluminum chloride (534 grams), 1,1-dimethyl-6-t-butylindane (1420 grams) and n-hexane (400 grams). The resulting reaction mass is poured into 5 liters of ice water with vigorous stirring thereby forming 2 liquid layers. The bottom (aqueous) layer is discarded and the organic layer is washed twice with 2 liters of water. Distillation affords recovered 1,1-dimethyl-6-t-butylindane (1252 grams, 62% recovery) and 878 grams of 4-acetyl-6-t-butyl-1,1-dimethylindane (90% yield based on acetyl chloride, 95% yield based on consumed 1,1-dimethyl-6-t-butylindane.).

EXAMPLE VII

5-Acetyl-1,1,2,3,3,6-Hexamethyl-1H-Indane

Reaction:

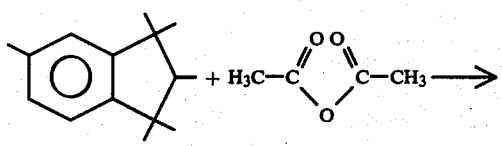

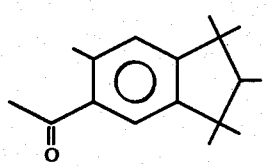

A solution of 1,1,2,3,3,6-hexamethyl-1H-indane (566 grams) and acetic anhydride (306 grams) is added over a 4 hour period at −10° C. to a slurry of aluminum chloride (534 grams), 1,1,2,3,3,6-hexamethyl-1H-indane (1050 grams) and isooctane (404 grams). The reaction is washed up as in Example #I. Distillation affords 395 grams of 5-acetyl-1,1,2,3,3,6-hexamethyl-1H-indane (54% yield based on charged AlCl$_3$) and 1192 grams of recovered 1,1,2,3,3,6-hexamethyl-1H-indane.

EXAMPLE VIII 1,1,4,4-Tetramethyl-6-Ethyl-7-Acetyl-1,2,3,4-Tetrahydronaphthalene Reaction:

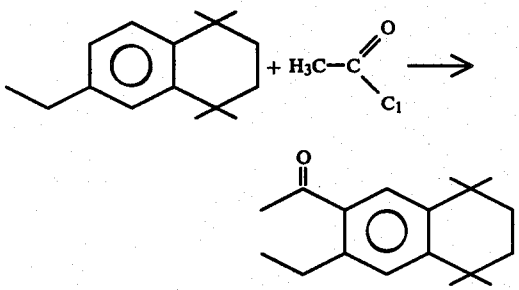

A solution of 1,1,4,4-tetramethyl-6-ethyl-1,2,3,4-tetrahydronaphthalene (528 grams) and acetyl chloride (234 grams) is added over a 3½ hour period at 70° C. to a well stirred slurry of aluminum chloride (534 grams), 1,1,4,4-tetramethyl-6-ethyl-1,2,3,4-tetrahydronaphthalene (1200 grams) and isooctane (432 grams). The reaction is worked up as in Example I to afford 689 grams of 1,1,4,4-tetramethyl-6-ethyl-7-acetyl-1,2,3,4-tetrahydronaphthalene (89% based on consumed 1,1,4,4-tetramethyl-6-ethyl-1,2,3,4-tetrahydronaphthalene) and 1106 grams of recovered 1,1,4,4-tetramethyl-6-ethyl-1,2,3,4-tetrahydronaphthalene.

What is claimed is:

1. A process for preparing an isochroman derivative having a structure selected from the group consisting of

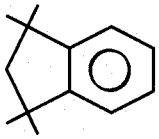

and

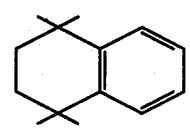

comprising the steps of reacting a hydrocarbon reactant which is an indane or tetrahydronaphthalene derivative having a structure selected the group consisting of:

with propylene oxide in the presence of a solvent consisting essentially of at least one aliphatic saturated $C_5$–$C_{10}$ hydrocarbon, said, aliphatic saturated hydrocarbon being halogen-free, at a temperature between −20° C. and −5° C. in the presence of an aluminum chloride catalyst; the weight ratio of the aliphatic saturated hydrocarbon to the indane or tetrahydronaphthalene derivative being from 1:10 up to 10:1; the mole ratio of aluminum chloride to propylene oxide being from 1:1 up to 2:1; the mole ratio of indane or tetrahydronaphthalene derivative to propylene oxide being from 1:1 up to 10:1; followed by addition of a lower $C_1$–$C_6$ alkanol at a temperature of −20° C. to 0° C.; the mole ratio of aluminum chloride to $C_1$–$C_6$ alkanol being from 2:1 up to 1:2; followed by addition at a temperature of from 20° C. up to 80° C. of a formaldehyde equivalent having the structure:

$$R'_{11}\text{—}O\text{—}CH_2\text{—}O\text{—}R'_{11}$$

wherein $R'_{11}$ represents $C_1$ to $C_6$ alkyl, or paraformaldehyde; and then quenching the resulting reaction mass by pouring it into water.

2. The process of claim 1 wherein the isochroman derivative prepared has the structure:

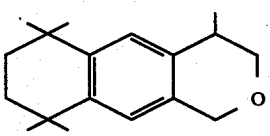

and the hydrocarbon reactant is a tetrahydronaphthalene having the structure:

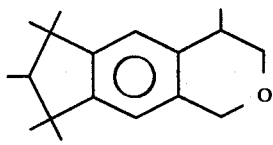

3. The process of claim 1 wherein the isochroman derivative produced has the structure:

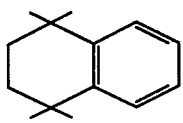

and the hydrocarbon reactant has the structure:

4. The process of claim 1 wherein the solvent used is selected from the group consisting of 2,2,4-trimethylpentane, n-hexane and n-octane.

5. The process of claim 4 wherein the solvent used is 2,2,4-trimethylpentane.

6. The process of claim 1 wherein the weight ratio of aliphatic saturated $C_5$–$C_{10}$ alkane hydrocarbon solvent: hydrocarbon reactant is from 0.2:1 up to 0.3:1 and the mole ratio of aluminum chloride:propylene oxide varies from 1:1 up to 1.02:1.

7. The process of claim 1 wherein the formaldehyde equivalent is selected from the group consisting of par-formaldehyde, di-isopropylformal and di-methoxy methane.

* * * * *